US007608274B2

(12) United States Patent
Ilan et al.

(10) Patent No.: US 7,608,274 B2
(45) Date of Patent: Oct. 27, 2009

(54) THERAPEUTIC PROCESSES AND USEFUL COMPOSITIONS THEREFOR

(75) Inventors: Yaron Ilan, Jerusalem (IL); Elazar Rabbani, New York, NY (US); Dean L. Engelhardt, New York, NY (US); Israel Gotsman, Jerusalem (IL); James J. Donegan, Long Beach, NY (US)

(73) Assignee: Enzo Therapeutics, Inc. c/o Enzo Biochem, Inc., Farmingdale, NY (US)

( * ) Notice: Subject to any disclaimer, the term of this patent is extended or adjusted under 35 U.S.C. 154(b) by 660 days.

(21) Appl. No.: 10/470,611

(22) Filed: Dec. 8, 2003

(65) Prior Publication Data
US 2005/0147586 A1   Jul. 7, 2005

Related U.S. Application Data

(63) Continuation of application No. 09/561,596, filed on Apr. 27, 2000, now abandoned.

(51) Int. Cl.
*A61K 39/29* (2006.01)
(52) U.S. Cl. ................................. 424/227.1; 424/189.1
(58) Field of Classification Search ........................ None
See application file for complete search history.

(56) References Cited

U.S. PATENT DOCUMENTS

| | | | |
|---|---|---|---|
| 5,272,065 | A | 12/1993 | Inouye et al. |
| 5,861,158 | A | 1/1999 | Kwak et al. |
| 5,958,681 | A | 9/1999 | Wetmur et al. |
| 6,297,048 | B1 | 10/2001 | Jolly et al. |
| 2001/0007153 | A1 | 7/2001 | Brown et al. |
| 2004/0022768 | A1 | 2/2004 | Roy-Chowdhury et al. |
| 2005/0118196 | A1 | 6/2005 | Ilan et al. |
| 2005/0136074 | A1 | 6/2005 | Ilan et al. |
| 2005/0147586 | A1 | 7/2005 | Ilan et al. |
| 2005/0255454 | A1 | 11/2005 | Ilan et al. |
| 2005/0260227 | A1 | 11/2005 | Ilan et al. |
| 2005/0260560 | A1 | 11/2005 | Ilan et al. |
| 2005/0277112 | A1 | 12/2005 | Ilan et al. |

FOREIGN PATENT DOCUMENTS

EP   1072271   7/2000

OTHER PUBLICATIONS

Saldinger et al (Gastroenterology 115:891-897).*
Ilan et al (Medical Hypotheses 52:505-509, 1999, in IDS).*
Ilan et al (Hepatology 27:1368-1376, May 1998).*
Gotsman et al (Gastroenterology 116:A1216-1217, 1999, in IDS).*
Czerkinsky et al (Immunological Reviews 170:197-222, 1999).*
Challacombe et al (Journal of Experimental Medicine 152:1459-1472, 1980).*
Benjamini, E., et al, editors, *Immunology: a Short Course*, Wiley-Liss, New York (1991).
Chisari, et al, "Hepatitis B virus immunopathogenesis," *Ann. Rev. Immunol.* 13:29-60.

Guidotti, et al, "Viral clearance without destruction of infected cells during acute HBV infection," *Science* 284:825-829 (1999).
Hauer, et al, "An analysis of interferon gamma, IL4, IL-5 and IL-10 production by ELISPOT and quantitative reverse transcriptase-PCR in human Peyer's patches," *Cytokine* 10:627-634 (1998).
Hollinger, et al, "Improved double antibody radioimmunoassay (RIA-D) methodology for detecting hepatitis B antigen and antibody," (Abstract only) *Am. Soc. Microbiol.* 72:213 (1972).
Ilan, et al, "Insertion of the Adenoviral E3 region into a recombinant viral vector prevents antiviral humoral and cellular immune responses and permits long term gene expression," *Proc. Natl. Acad. Sci. USA* 94:2587-2592 (1997).
Ilan, et al, "Oral tolerization to adenoviral antigens permits long term gene expression using recombinant adenoviral vectors," *J. Clin. Invest.* 99:966-973 (2000).
Ilan, et al, "Treatment of experimental colitis by oral tolerance induction: a central role for suppressor lymphocytes," *Am. J. Gastroenterol.* 95:966-973 (2000).
Ishikawa, et al, "Polyclonality and multispecificity of the CTL response to a single viral epitope," *J. Immunol.* 161:5842-5850 (1998).
Larsson, et al, "A recombinant vaccinia virus based ELISPOT assay detects high frequencies of Pol-specific CD8 T cells in HIV-1-positive individuals," *AIDS* 13:767-777 (1999).
Rehermann, et al, "Cytotoxic T lymphocyte responsiveness after resolution of chronic hepatits B virus infection," *J. Clin. Invest.* 7:1655-1665 (1996).
Shouval, et al, "Comparative morphology and tumorigenicity of human hepatocellular cell carcinoma lines in athymic rats and mice," *Vichow's Archives A. Path. His.* 412:595-606.
Shouval, et al, "Adoptive transfer of immunity to hepatitis B virus in mice following bone marrow transplantation through immunization of bone marrow donors," *Hepatology* 17:955-959 (1993).
Sigal, LH, et al, *Immunology and Inflammation: Basic Mechanisms and Clinical Consequences*, McGraw Hill, New York, p. 528 (1994).
Stites, DP, et al, *Basic and Clinical Immunology*, Appleton & Lange, Norwalk, CT (1991).

(Continued)

*Primary Examiner*—Mary E Mosher
(74) *Attorney, Agent, or Firm*—Ronald C. Fedus, Esq.

(57) ABSTRACT

This invention provides novel processes for therapeutic applications, including the treatment of subjects carrying infectious agents or having impaired autoimmunity or impaired immune condition. The therapeutic applications disclosed herein are also directed at the treatment of cancerous subjects with malignant tumors containing cancerous cells or malignant or cancerous cells. Vaccination processes for preventing infections in subjects are also provided. The novel processes comprise introducing into or administering to a subject one or more antigens, or trained or adopted immune cells. These antigens or immune cells are capable of establishing or increasing at least one first specific immune response and decreasing at least one second specific immune response. Such responses include components, such as cellular immune reaction elements, humoral immune reaction elements and cytokines, the latter also encompassing interferons and lymphokines. Useful compositions are also provided by this invention.

7 Claims, No Drawings

OTHER PUBLICATIONS

Weiner, HL, et al, editors, "Oral Tolerance: Mechanisms and Applications," *Annals of the New York Academy of Sciences 778* (1996).

Bretscher, et al, "Distinct immunological states in murine cutaneous leishmaniasis by immunising with different amounts of antigen: the generation of beneficial, potentially harmful, harmful and potentially extremely harmful states," (Abstract only) *Behring Inst. Mitt. 98*:153-159 (1997).

Ahuja, S.S., et al., "Human Dendritic Cell (DC)-Based Anti-Infective Therapy: Engineering DCs to Secrete Functional IFN-y and IL-12," *J. Immunol. 161*:868-876 (1998).

Chow, Y-H, et al., "Development of Th1 and Th2 Populations and the Nature of Immune Response to Hepatitis B Virus DNA Vaccines Can be Modulated by Codelivery of Various Cytokine Genes," *J. Immunol. 160*:1320-1329 (1998).

Ribas, A., et al., "Immune Deviation and Fas-mediated Deletion Limit Antitumor Activity after Multiple Dendritic Cell Vaccinations in Mice," *Cancer Research 60*:2218-2224 (2000).

Waris, M.E., et al., "Respiratory Syncytial Virus Infection in BALB/c Mice Previously Immunized with Formalin-Inactivated Virus Induces Enhanced Pulmonary Inflammatory Response with a Predominant Th2-Like Cytokine Pattern," *J. Virology 70*:2852-2860 (1996).

Gotsman, I., et al., "Oral Tolerance Towards Hepatitis B Antigens in a Murine Model," *Gastroenterology 116*:A1216-A1217 (1999).

Gotsman, I., et al., "Induction of Oral Immune-Regulation Towards Hepatitis B Virus Envelope Proteins Suppresses the Growth of Hepatocellular Carcinoma in Mice," *Hepatology 32*:206A (2000).

Gotsman, I., et al., "Induction of oral tolerance towards hepatitis B envelope antigens in a murine model," *Antiviral Research 48*:17-26 (2000).

Gotsman, I., et al., "Downregulation of a tumor promotion immune response via induction of oral tolerance towards tumor-associated-antigens: can we 'eat the tumor?'," *Medical Hypotheses 56*:487-492 (2001).

Ilan, Y., et al., "Induction of tolerance to hepatitis B virus: can we 'eat the disease' and live with the virus?," *Medical Hypotheses 52*:505-509 (1999).

Ilan, Y., et al., "Induction of oral Tolerance in splenocyte recipients toward pretransplant antigens ameliorates chronic graft versus host disease in a murine model," *Blood 95*:3613-3619 (2000).

Nagler, A., et al., "Oral Tolerization Ameliorates Liver Disorders Associated with Chronic Graft Versus Host Disease," *Hepatology 28*:403A (1998).

Safadi, R., et al., "Oral Immune-Regulation Towards Hepatitis B Virus Proteins. A New Mode of Treatment for Chronic HBV Infection: Results of a Phase 1 Clinical Trial," *Hepatology 32*:379A (2000).

Saldinger et al., Immunization of BALB/C Mice With Helicobacter Urease B Induces A T Helper 2 Response Absent . . . Gastroenterology 1998;115:891-897.

Ilan et al., Oral Tolerization to Adenoviral Proteins Permits Repeated Adenovirus-Mediated Gene Therapyin Rats . . . Hepatology 1998;27:1368-1376.

Diepolder et al., Anergic TH1 Clones Specific for Hepatitis B Virus (HBV) Core Peptides . . . J. of Virology 1996, vol. 70, No. 11, pp. 7540-7548.

Furuta et al., Clinicopathologic Features of Hepatocellular Carcinoma in Young Patients, Cancer 1990, 66: 2395-2398.

Ilan et al., Induction of Tolerance to Hepatitis B Virus: Can We 'Eat the Disease' and Live With the Virus, Medical Hypotheses 1999; 52(6): 505-509.

Safadi et al., Induction of Oral Immune Regulation Towards Liver-Extracted Proteins for Treatment of Chronic HBV and . . . Liver International 2004; 24:295-307.

Soiffer et al., Prediction of Graft-Versus-Host Disease by Phenotypic Analysis of Early . . . Blood 1993, vol. 82, No. 7, pp. 2216-2223.

Ustun et al., Hepatitis B Virus Infection in Allogenic Bone Marrow Transplantation, Bone Marrow Transplantation 1997, 20:289-296.

Shouval et al., Adoptive Transfer of Immunity to Hepatitis B Virus in Mice by Bone Marrow Transplantation From Immune Donors, Hepatology 1993; 17: 955-959.

Safadi et al., Treatment of Chronic Heatitis B Virus Infection Via Oral Immune Regulation Toward Hepatitis B Virus Proteins, Am J Gastroenterol 2003; 98: 2505-2515.

Bretscher et al., Distinct Immunological States in Murine Cutaneous Leishmaniasis by Immunising With Different Amounts of Antigen . . . Behring Inst Mitt 1997 Feb. 98: 153-159.

Gotsman et al., Oral Tolerance Towards Hepatitis B Antigens in a Murine Model, Gastroenterology, 116:A1216-A1217, 1999.

Shimizu et al., Dendritic Cell Immunization Breaks Cytotoxic T Lymphocyte Tolerance in Hepatitis B Virus Transgenic Mice, J. of Immunology, 1998;161: 4520-4529.

Tan et al., Rapid Death of Adoptively Transferred T Cells in Acquired Immunodeficiency Syndrome, Blood, vol. 93, No. 5, 1999, pp. 1506-1510.

Darcy et al., Redirected Perforin-Dependent Lysis of Colon Carcinoma by Ex Vivo Genetically Engineered CTL, J. of Immunology, 2000; 164: 3705-3712.

Walton et al., Tumor Factor-Alpha and Interferon-Gamma Reduce Prolactin Release in Vitro, Am J Physiol 259(22):E672-E676, 1990.

Hadziyannis et al., New Developments in the Treatment of Chronic Hepatitis B, Expert Opin. Biol. Ther., 2006; 6(9):913-921.

Guidotti et al., High-Level Hepatitis B Virus Replication in Transgenic Mice, Journal of Virology, 1995, vol. 69, No. 10, pp. 6158-6169.

* cited by examiner

THERAPEUTIC PROCESSES AND USEFUL COMPOSITIONS THEREFOR

CROSS-REFERENCE TO RELATED APPLICATIONS

This is a continuation of U.S. patent application Ser. No. 09/561,596, filed on Apr. 27, 2000, now abandoned.

FIELD OF THE INVENTION

This invention relates to the field of therapeutic processes and therapeutic compositions, including treatments and compositions directed against infectious agents, cancerous conditions and immunity disorders. This invention also relates to therapeutic processes and compositions in vaccination and immunization.

All patents, patent applications, patent publications, scientific articles and the like, cited or identified in this application are hereby incorporated by reference in their entirety in order to describe mom fully the state of the art to which the present invention pertains.

BACKGROUND OF THE INVENTION

Antigenic stimulation of the immune system induces a series of reactions which can be mediated by immunological components such as the humoral, cellular or cytokine responses. The directionality of these reactions can be considered to be of a reactive or suppressive nature. For instance, in the context of the present invention, an immune reaction is defined as a response that specifically neutralizes, reduces or eliminates the presence of a specific antigen or set of antigens in a subject. In the context of the present invention, immune suppression is defined as a response that specifically diminishes or reduces an immune reaction or has the capability of blocking an immune reaction from being initiated. Examples of humeral responses that may contribute to an immune reaction can comprise or not be limited to the production of antibodies or proteins involved in complement fixation. Examples of cellular responses that may contribute to an immune reaction can comprise but not be limited to expansion of helper T cells, Natural killer (NK) cells, cytopathic T-lymphocytes (CTLs) and B lymphocytes. Examples of cytokine responses that may contribute to an immune reaction can comprise but not be limited to induction of IFN y and IL-2. Examples of humoral responses that may contribute to an immune suppression reaction can comprise or not be limited to the production of anti-idiotypic antibodies. Examples of cellular responses that may contribute to an immune suppression reaction can comprise but not be limited to expansion of supressor T-cells. Examples of cytokine responses that may contribute to an immune suppression reaction can comprise but not be limited to induction of TGF $\beta$, IL-4 and IL-10

The stimulation or manipulation of the immune system can be achieved by the introduction of an antigen or antigens that are foreign to the subject. This reaction is a major source of the body's resistance to colonialization by viral, bacterial or parasitic organisms. The absence of this defense in immunocompromised individuals has allowed what are called opportunistic infections i.e. infections by organisms that are normally non-pathogenic. Examples of such individuals are patients undergoing chemotherapy or transplantation, AIDS patients and individuals with severe combined immune deficiency. Reactivity to foreign antigen sources is also the source of allergy immune reactions, i.e. immunostimulation caused by exposure to antigenic substances present in the environment including dust, pollen, hair and other materials.

Immune stimulation can also be induced by substances that are native to the subject or are immunologically related to native antigens. An illustrative example of this are antigens that provoke autoimmune responses. Since reactivity to the cells, tissues and organs that make up an organism would be self-destructive, there is a system of control over the induction of this form of immune reactions. The mechanism that is most widely regarded as responsible for this self-limitation has been called clonal deletion. In this model, cells that are stimulated by self-antigens are selectively eliminated in a process that begins shortly after birth. After a certain amount of time, the repertoire of immunogenic responses that remains is devoid of cells capable of responding to these native stimuli. Since clonal deletion is an irreversible process, the existence of auto-immunity has been ascribed to a limited number of cells that were unable to achieve a "threshold" level of stimulation by native antigens. Then at some later point in life when clonal elimination processes were absent, an event or events have occurred that induced a heightened immune response to native antigens.

Other example of an immune response to a native antigen is recognition of tumor antigens. The "immune surveillance" theory proposes that during the course of a lifetime, potentially tumorogenic cells are constantly arising, but they are recognized and purged by immune processes. Although proteins expressed by these cells are derived from the genetic information of the subject, recognition as antigens may still take place when they are mutated or inappropriately expressed in a subject. Growth of a tumor may then take place when there is somehow a breakdown in this surveillance process.

Varying degrees of immune response to antigens are seen both in terms of the intrinsic nature of the particular antigens and also in terms of the individual response of a subject to their presence. A given antigen may comprise a single immunostimulatory epitope or it may comprise a number of epitopes, each of which has its own potential level of immunostimulatory effect. Stimulatory activity of an antigen may also be increased by the use of a supplementary treatment called an adjuvant.

The series of events created by the presence of a particular antigen in a subject is typically described in reviews and textbooks on Immunology as leading to generation of a singular immune state. For example, in immunization a specific humoral and/or cellular response against the immunogen is induced. This "mono-static" view predicts mutually exclusive results of either a state of immune responsiveness or a state of immune suppression. In prior art, attempts at alteration of a pre-existing immune state are still of a unidirectional nature. These have been used either for the purpose of extending or boosting a particular immune response or leading to the reversal or suppression of the immune response. With reference to a particular immune target, either case is a change from one particular singular state to a different singular state. Thus, it would be predicted that treatments that lead to reduction or elimination of any aspect of immune reactivity towards a pathogen should result in allowance of further progression in either expression or growth of the pathogen by releasing the pathogen from immune control. This point has been discussed previously in a pending patent application, U.S. Ser. No. 08/808,1629 filed Feb. 28, 1997 which is incorporated by reference in its entirety, where it was suggested that drug treatments suitable for the pathogen would have to be used in conjunction with an immune therapy treatment. However, the drawback of a need for such dual therapeutic or pathogen management procedures was considered to be outweighed by benefits that would be provided by the reduction of immune responses that contribute to aspects of the disease state. Examples of such undesirable immune derived aspects are the inflammation and tissue destruction that are the hallmarks of chronic HBV and HCV infection. Thus, according to previous views a decrease in undesirable immune reactivity should also induce a decrease in other immune responses that may be beneficial for the continued health of the subject.

SUMMARY OF THE INVENTION

The present invention provides a treatment process for subjects, i.e., a human subject, carrying an infectious agent. The process comprises introducing into or administering to the subject one or more antigens. Such antigens are characterized in being capable of (1) establishing or increasing at least one first specific immune reaction directed against (i) the infectious agent, or (ii) cells infected with the infectious agent, or (iii) a combination of (1)(i) and (1)(ii). These antigens are further characterized in being capable of (2) decreasing at least one second specific immune reaction which is different from the first specific immune reaction (a)(1), the second specific immune reaction itself being directed toward (i) the infectious agent, or (ii) cells infected with the infectious agent; or (iii) uninfected cells; or (iv) a combination of any of (2)(i), (2)(ii) and (2)(iii) just mentioned.

The present invention also provides a process of treating a subject carrying an infectious agent. In this aspect of the invention, the process comprises the steps of (a) introducing into or administering to the subject at least two different antigens, each of these antigens being capable of (1) establishing or increasing at least one first specific immune reaction directed against:(i) the infectious agent; or (ii) cells infected with the infectious agent; or (iii) a combination of (1)(i) and (1)(ii) just described. The antigens are further capable of (2) decreasing at least one second specific immune reaction which is different from the first specific immune reaction (a)(1). The second specific immune reaction is itself directed toward (i) the infectious agent; or (ii) cells infected with the infectious agent; or (iii) uninfected cells; or (iv) a combination of any of (2)(i), (2)(ii) and (2)(iii) just described.

Also provided by the present invention is a process of treating a subject carrying an infectious agent in which immune cells are usefully trained or adopted. Here, the steps involve (a) removing immune cells from said subject, (b) training or adopting said removed cells, (c) introducing into or administering to the subject the immune cells which have been trained or adopted, e.g., in vivo or in vitro. Such immune cells are capable of (1) establishing or increasing at least one first specific immune reaction directed against:(i) the infectious agent; or (ii) cells infected with the infectious agent; or (iii) a combination of (1)(i) and (1)(ii) just described. The immune cells are also capable of (2) decreasing at least one second specific immune reaction which is different from the first specific immune reaction (a)(1). The second specific immune reaction is directed toward:(i) the infectious agent; or (ii) cells infected with the infectious agent; or both of the foregoing.

Still provided by this invention is a process of treating a subject carrying an infectious agent, the process utilizing immune cells and multiple steps. First, immune cells are removed from a trained donor, or from a naive donor wherein the immune cells have been trained in a surrogate or in vitro. Second, the removed immune cells are introduced into or administered to the subject. These immune cells are characterized in being capable of (1) establishing or increasing at least one first specific immune reaction directed against (i) the infectious agent; or (ii) cells infected with the infectious agent; or (iii) a combination of (1)(i) and (1)(ii) just described. The immune cells are also capable of (2) decreasing at least one second specific immune response which is different from the first specific immune reaction (a)(1). Here, the second specific immune response is directed toward (i) the infectious agent; or (ii) cells infected with the infectious agent; or (iii) uninfected cells; or (iv) a combination of any of (2)(i), (2)(ii) and (2)(iii) as just described. Finally, the subject is managed, monitored or treated for graft-versus-host complications.

Another process provided herein is a process for treating a cancerous subject who could have such cancer in the form of a tumor containing cancerous cells, or in the form of cancerous cells. This process comprises the step or steps of (ay introducing into or administering to the subject one or more specific antigens which are capable of two significant functions. First, these specific antigens are capable of (1) establishing or increasing at least one first specific immune reaction directed against (i) cancer associated antigens; or (ii) cancerous cells; or (iii) a combination of (1)(i) and (1)(ii) just described. These specific antigens are also capable of (2)decreasing at least one second specific immune reaction which is different from the first specific immune reaction, in that the second specific immune reaction is directed toward (i) any cancer associated antigens; or (ii) any cancerous cells; or (iii) any non-cancerous cells; or (iii) a combination of these last three elements.

Another useful process provided by this invention involves treating a cancerous subject who has a tumor containing cancerous cells, or who has cancerous cells. Here, the process comprising the steps of (a) removing immune cells from the cancerous subject, (b) training or adopting said removed cells, (c) introducing into or administering to said subject said immune cells which have been rendered capable of (1) establishing or increasing at least one first specific immune reaction directed against (i) cancer associated antigens; or (ii) cancerous cells; or (iii) a combination of (1)(i) and (1)(ii) just described. The immune cells are further capable of (2) decreasing at least one second specific immune reaction which is different from the first specific immune reaction (a)(1). This second specific immune reaction is directed toward (i) the cancer associated antigens; or (ii) the cancerous cells; or (iii) non-cancerous cells; or (iii) a combination of (2)(i), (2)(ii) and (2)(iii) just described.

Another process provided herein is useful for treating a cancerous subject who has a tumor containing cancerous cells, or who has cancerous cells. This process comprises the first step of (a) removing immune cells from a trained donor, or from a naive donor wherein the immune cells have been trained in a surrogate or in vitro. The next step involves (b) introducing into or administering to the subject the immune cells which were removed. The immune cells have been rendered capable of (1) establishing or increasing at least one first specific immune reaction directed against (i) cancer associated antigens; or (ii) cancerous cells; or (iii) a combination of (1)(i) and (1)(ii) as just described. The immune cells are further capable of (2) decreasing at least one second specific immune response which is different from the first specific immune reaction (a)(1). The second specific immune response is directed toward (i) cancer associated antigens; or (ii) cancerous cells; or (iii) non-cancerous cells; or (iii) a combination of (2)(i), (2)(ii) and (2)(iii) as just described. The next step of the process calls for (c) managing or treating the subject for graft-versus-host complications.

Another process is provided for enhancing the immunized state of a subject vaccinated against an infectious agent. This process comprises the step or steps of (a) introducing into or administering to the subject one or more specific antigens, such antigen or antigens being capable of (1) establishing or increasing at least one first specific immune reaction directed against the infectious agent; and (2) decreasing at least one second specific immune reaction which is different from the first specific immune reaction (a)(1). The second specific immune reaction is directed toward (i) the infectious agent; or (ii) uninfected cells; or (iii) a combination of (2)(i) and (2)(ii) just described.

Another process is useful for enhancing the immunized state of a subject vaccinated against an infectious agent. Here, the process comprises the steps of: (a) removing immune cells from the subject, (b) training or adopting the cells so removed, and (c) introducing into or administering to the subject these immune cells which have been rendered capable of two significant biological functions. First, the immune cells are capable of (1) establishing or increasing at least one first specific immune reaction directed against the infectious agent; and (2) decreasing at least one second specific immune reaction which is different from the first specific immune reaction (a)(1). The second specific immune reaction is directed toward (i) the infectious agent: or (ii) uninfected cells; or (iii) a combination of (2)(i) and (2)(ii) as just described.

Still yet another process is useful for enhancing the immunized state of a subject vaccinated against an infectious agent. This process comprises the steps of (a) removing immune cells from a trained donor, or from a naive donor wherein the immune cells have been trained in a surrogate or in vitro, and (b) introducing into or administering to the subject the removed immune cells which have been rendered capable of two significant biological or immunological functions. First, these immune cells are capable of (1) establishing or increasing at least one first specific immune reaction directed against the infectious agent, and (2) decreasing at least one second specific immune reaction which is different from said the specific immune reaction (a)(1). This second specific immune reaction is directed toward (i) the infectious agent; or (ii) uninfected cells; or (iii) a combination of the last-described elements, (2)(i) and (2)(ii). Another step in this process involves (c) managing or treating said subject for graft-versus-host complications.

Another process herein is useful for vaccinating a subject against an infectious agent, this process comprising the steps of (a) introducing into or administering to the subject one or more first antigens capable of establishing an immune response against the infectious agent; and (b) introducing into or administering to the subject one or more second specific antigens capable of: (1) establishing or increasing at least one first specific immune reaction directed against the infectious agent; and (2) decreasing at least one second specific immune reaction which is different from the first specific immune reaction (a)(1), the second specific immune reaction being directed toward (i) the infectious agent; or (ii) uninfected cells; or both.

Yet another useful process is directed toward vaccinating a subject against an infectious agent, the process comprising the steps of (a) introducing into or administering to the subject one or more first antigens capable of establishing an immune response against the infectious agent; and (b) introducing into or administering to the subject immune cells capable of (1) establishing or increasing at least one first specific immune reaction directed against the infectious agent; and (2) decreasing at least one second specific immune reaction which is different from the first specific immune reaction (a)(1), this second specific immune reaction being directed toward (i) the infectious agent; (ii) uninfected cells, or both. In this process, the immune cells have been removed from the subject and otherwise trained or adopted prior to the aforementioned introducing or administering step (b).

Another process for vaccinating a subject against an infectious agent comprises the steps of (a) introducing into or administering to the subject one or more first antigens capable of establishing an immune response against the infectious agent, (i) introducing into or administering to the subject immune cells capable of (1) establishing or increasing at least one first specific immune reaction directed against the infectious agent; and (2) decreasing at least one second specific immune reaction which is different from the first specific immune reaction (a)(1), the second specific immune reaction being directed toward (i) the infectious agent; or (ii) uninfected cells, or both. Notably, prior to the introducing or administering step (b), the immune cells have been removed from a trained donor, or from a naive donor wherein the immune cells were trained in a surrogate or in vitro. Another step of this process calls for (c) managing or treating the subject for graft-versus-host complications.

Also provided by the present invention are useful compositions of matter. These include the following a therapeutic composition of matter comprising specific antigens capable of (1) establishing or increasing at least one first specific immune reaction directed against an infectious agent of interest, cells infected with the infectious agent, or both, and (2) decreasing at least one second specific immune reaction which is different from the first specific immune reaction, the second specific immune reaction being directed toward the infectious agent, cells infected with the infectious agent, uninfected cells, or a combination of any of the infectious agent, the infected cells and the uninfected cells.

Another therapeutic composition of matter comprises trained or adopted immune cells capable of (1) establishing or increasing at least one first specific immune reaction directed against an infectious agent of interest, cells infected with the infectious agent, or both, end (2) decreasing at least one second specific immune reaction which is different from the first specific immune reaction, the second specific immune reaction being directed toward the infectious agent, cells infected with the infectious agent, uninfected cells, or a combination of any of the infectious agent, infected cells and uninfected cells.

Another therapeutic composition of matter comprises trained or adopted immune cells capable of (1) establishing or increasing at least one first specific immune reaction directed against cancer associated antigens, cancerous cells, or a combination of the cancer associated antigens and the cancerous cells; and (2) decreasing at least one second specific immune reaction which is different from the first specific immune reaction, the second specific immune reaction being directed toward the cancer associated antigens; cancerous cells; non-cancerous cells; or a combination of cancer associated antigens, cancerous cells and non-cancerous cells.

Further yet is a therapeutic composition of matter comprising trained or adopted immune cells capable of (1) establishing or increasing at least one first specific immune reaction directed against cancer associated antigens; cancerous cells; or a combination of such cancer associated antigens and cancerous cells; and (2) decreasing at least one second specific immune reaction which is different from the first specific immune reaction (1), the second specific immune reaction being directed toward the cancer associated antigens; cancerous cells, non-cancerous cells, and a combination of cancer associated antigens, cancerous cells and non-cancerous cells.

BRIEF DESCRIPTION OF THE FIGURES

No figures

DETAILED DESCRIPTION OF THE INVENTION

The present invention provides for novel methods and compositions that when introduced into a subject having a particular immune state towards a given immune target, can achieve a new state which exhibits not only more than one change in said state, but these changes are in more than one direction. Such a dual or multi-faceted alteration in a given immune state may lead to an overall enhancement of immune response towards immunological targets such as infectious agents or cancer cells. Furthermore, these methods and compositions may provide reduction or elimination of undesirable consequences in the initial immune state towards the immune target.

A novel and unanticipated result of the present invention is that introduction of a viral antigen to an infected subject can achieve an alteration of the immune state that comprises both a decrease in one or more immune reactions towards antigens carried by the pathogen or related cellular targets and simultaneously a display of one or more enhanced or increased specific immune reactions towards said immunological target. Prior art is incapable of either predicting or explaining such a dual response. As described previously, prior art predicts that the introduction of a viral antigen into an infected subject should lead to a single change in the immunological state towards the infectious agent, either enhancement of the immune reaction or loss of immune reactivity.

The prior view that immune reactive state towards a particular immune target is not only monostatic but a given manipulation of immunological systems that can change over state would only lead to a new immunological state that again is monostatic. To put this in other words, in immunological processes that change, a given specific immune are perceived or intended to be unidirectional in character; thus, they could only lead to a single new immunological state (new response or no response).

The present invention provides novel methods and compositions that when introduced into a subject carrying an infectious agent having an immune state directed towards the infectious agent, the said novel methods and compositions are capable of producing a dual effect of a decrease or inversion of at least one component of the immune response towards an epitope or antigen carried by the infectious agent and simultaneously and in the opposite direction and enhancement or increase in the immune response to an epitope or antigen of the same epitope. The decrease, inversion, enhancement or increase may be directed towards different epitopes or antignes or they may be the same antigen. When they are the same epitope or antigen the simultaneous presence is carried out by different components of the immune reaction.

In contrast to this prediction, it has now been demonstrated that oral introduction of HBV antigens into infected subjects simultaneously gave indications of both a decrease in specific immune reactivity towards HBV antigens and related immunological targets such as hepatocytes and an increase in other specific immune reactions towards HBV antigens. The simultaneous presence of these apparently antagonistic effects was independently measured by various parameters and components of the immune system. For instance, evidence for a loss or diminishment of immune reactivity towards viral antigens in the subjects could be observed by a decrease in enzyme activities (ALT and AST) and histology markers associated with liver inflammation and tissue destruction. In contrast to previous views that would have predicted a proliferation of viral activity when immune reactivity towards the immunological target was decreased, the subjects unexpectedly also showed evidence of enhanced immune reactivity towards virus antigens. Markers that demonstrated the simultaneous presence of this surprising increase in the specific immune response towards the virus included induction of antigen-specific T cell proliferation responses, antiviral cytokine synthesis (as measured by ELISA and RT-PCR assays of IFN γ) and antigen-specific CTL responses. Lastly and most notably virus copy number measurements showed that instead of an increase in viral load, in some subjects there were decreases as large as three orders of magnitude lower than initial levels. This drop in viral loads indicates that even after a decrease in some elements of immune reactivity towards HBV antigens there are other components of the immune system that are capable of providing an increased immune response that has either inhibited viral production or enhanced virus clearance. Thus the present invention provides a binary immune response that can provide decreased immune reactivity that should ameliorate the chronic inflammation that is responsible for liver damage in chronic HBV infection and at the same time the present invention provides for an increased immune reaction towards the virus that can decrease the viral load. The present invention can find utility in other infections where a complex change in immune reactions is desired rather than a unitary effect of either a gain or loss in immune reactivity. In addition to HBV, other pathogens that may benefit from application of the present invention can comprise but not be limited to: HCV, HIV, HTLV, CMV, herpes and herpes zoaster, varicella, EBV, chronic fatigue syndrome, (with and without EBV infections). STD, bacterial infections (with immune mediated phenomena such as endocarditis or sepsis), mycobacteria, rickettsia, fungi and parasites.

The unexpected and unanticipated result of a duality in the immune response in an infected subject with a decrease in at least one immune reaction while simultaneously demonstrating an enhanced immune reaction to the pathogen could be explained further. In this view, immunological manipulations do not lead to a unidirectional change in immune reactivity or immune response but rather a bi-directional effect that can simultaneously increase or decrease the effects of various elements or components of immune response to different extents or directions. Thus, in immunogical systems there can be an effector that can act as an inversion factor with regard to immune reactivity, immune suppression or both that can lead to induction of a dual response. These different responses can be manifested through different elements or components of the immune system such as the humoral, cellularor cytokine responses or through two different epitopes of the same immunological target.

Another aspect of the present invention is directed towards immune manipulation prior to infection by a pathogen for vaccination purposes. For some infective agents, prevention by immunological means has been a failure. Notable examples of this have been attempts at vaccination against HCV and HIV. In contrast to prior art where only induction or enhancement of immune reactivity was undertaken, the present invention recognizes and uses the binary effect of immune manipulation to provide a more effective immune response towards these potential pathogens. The present invention carries this out by providing a reduction of specific immune reactivity towards one or more antigens of a pathogen while also providing an induction or increase in the immune reactivity towards one or more antigens of the pathogen. In other words, the present invention teaches that in order to achieve an overall stronger immune response towards a pathogen or immunological target, one has to decrease at least one aspect of the undesirable immune response in a subject. For example, a subject could be immunized against a target virus by injection of an antigen with or without an adjuvant. After a specific immune state has been established, the same or different antigens are orally introduced into the subject such that a decrease of at least one immune reaction towards the immunological target takes place while achieving an increase in the immune reactivity towards the pathogen. This seemingly antagonistic effect could take place either simultaneously or sequentially. The subject may be further treated with other immunological manipulations that may increase the overall immune responsiveness to the pathogen. It can be seen that this example is actually a parallel to the previously described therapy for HBV infection that resulted in a heightened immune response after oral administration of HBV antigens to HBV infected subjects.

Another aspect of the present invention is directed towards manipulation of the immune response towards tumors for management of cancer. As described previously, recognition by the immune system of cancer cells as being "foreign" is believed to be one of the mechanisms of prevention of tumor growth. Thereby, the continued presence and growth of cancerous cells in a subject represents a lapse, defect or suppression of the immune surveillance program. One factor that may be involved in this "escape" process is the induction of cytokines or other cellular factors that inhibit the expansion or immune reactivity of T-cells towards the malignant cells. Previous attempts have had a limitation that their efforts to heighten immune reactivity has been negated by an increased induction of these factors. For some tumors, there is the paradoxical effect that the higher the degree of immune reactivity, the faster the tumor is able to grow (L. H. Sigal and Y. Ron in Immunology and Inflammation: Basic Mechanisms and Clinical Consequences, page 528 McGrawHill, Inc, NY, N.Y., 1994).

Chronic infection by HBV has been discussed earlier in the context of viral infection. One of the reasons that this is a matter of concern is due to the increased likelihood of development of hepatocellular carcinoma (HCC). Hepatocellular carcinoma rate is increasing worldwide, especially in-patients with chronic viral hepatitis. Currently there is no effective treatment for this malignant neoplasm, and the prognosis is limited. The mechanism of HCC development and the exact role of Hepatitis B virus (HBV) in tumor induction are not well understood. Approximately one third of patients with HBV associated HCC express the HBV envelope antigen (HBsAg) on their cell surface which in this particular situation, may serve as a tumor associated antigen. Patients with persistent HBV infection have a defective or deviant immune response against the virus that not only fails to clear it, but there is a pathological immune response such as induction of severe liver injury and a potential role in enablement of neoplasm growth.

It has previously been shown that oral tolerance towards adenoviral antigens effectively can prevent an anti-viral immune response (U.S. patent application Ser. No. 08/808, 629, supra). In addition, adoptive transfer of tolerance by transplantation of immune cells from orally tolerized donors to sublethally irradiated recipients, supports the existence of suppresser cells in this setting. Previously oral tolerance was shown to induce antigen-specific immune suppression of HBsAg by feeding HBV antigens (U.S. patent application Ser. No. 08/808/629 supra). Therefore, adoptive transfer of this immune suppression should cause immune hyporesponsiveness to HBsAg via suppressor cells. In the case of HCC expressing HBsAg, the HBV antigen may be considered a tumor associated antigen. Based on prior art that has been cited previously, it would have been predicted that a decrease in a specific immune response to tumor cells or tumor associated antigens would allow unbridled growth of tumors.

Contrary to this expectation, the present invention demonstrates that it is possible to manipulate the immune system such that an effective immune response is achieved or enhanced towards malignant cells while exhibiting a decrease in other aspects of the immune response towards cancerous cells. This binary effect was evident in experiments where donor immune cells were implanted into recipient mice carrying human cancerous cells. Without donor cell implantation these mice showed numerous malignant growths and early death (group D in Example 2). In contrast, when the donor immune cells were trained by inoculation of HBV antigens prior to implantation, no evidence of tumor growth was seen (Group C in Example 2). Moreover, if the donor cells were given a dual treatment of oral administration of antigens as well as the inoculation, a binary immune response was observed (Groups A and B in Example 2). Evidence of a decrease in immune reactivity in these last two groups was demonstrated by reduced levels of anti-HBs antibodies as compared to the control. The presence of an immune reaction to the HBV and/or cancer antigens was demonstrated by the eventual disappearance of a marker for the tumor (AFP) and lack of any macroscopic evidence for the presence of tumor growth. Evidence for an enhanced immune reaction in Groups A and B was seen by the increase in the levels of IFNγ compared to Group C which was treated with only inoculation. These results demonstrate that immunological manipulation can lead to a reduction of a specific immune reaction towards tumor specific antigen or antigens (lowering antibody levels) while achieving an enhancement of an antigen specific immune reaction (increase in IFNγ levels). Even in the presence of reduced levels of antibodies, there was prevention of tumor growth thereby demonstrating the ability of the enhanced immune response to manage cancer cells. This treatment may thereby reduce undesirable immune components or elements such as suppressor cells or cytokines that promote tumor growth and allow an enhanced immune reactivity towards the tumor.

Malignancies that may find utility in the present invention can comprise but not be limited to Hematological malignancies (including leukemia, lymphoma and myeloproliferative disorders), Hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Karposi).

Induction of the extent and nature of an immune response can be determined by a number of factors. Illustratively, these can comprise the nature of an antigen, modifications of an antigen, the amount of an antigen, the method of introduction of an antigen into the subject, application of secondary treatments and other methods that are well known in the art. Antigens can be prepared from biological sources or they can be obtained synthetically or from recombinant DNA technology. Antigens from biological sources can be derived from cells, cell extracts, cell membranes and biological matrixes.

The form of the antigen may present opportunities for manipulations of immune response. For example bovine γ globulin (BGG) in saline solution results in an immune state characteristic of an immunoreactive response. However, if the same solution of BGG is separated out into monomeric and polymeric forms, the monomeric form can actually be seen to induce tolerance while the polymeric forms maintains properties that result in an immune reactivity response (pg. 304 in Immunology: a Short Course, E. Benjamini and S. Leskowitz, Eds. Wiley-Liss, NY, N.Y., USA). It should also be pointed out that the unfractionated solution should be viewed as a balance of immune reactive and immune suppressive factors where the immune reactive potential is stronger in this experimental system. Therefore, polymerization and degradation, fractionation and chemical modification, are all capable of altering the properties of a particular antigen in terms of potential immune responses.

Antigens have been discussed as if each was a singular homogeneous entity, but although an antigen may comprise a single epitope it may also comprise a number of different epitopes. The particular properties of each epitope of an antigen may be dissimilar, this is reflected in the immune response to an antigen where there may be particularly strong responses to some epitopes and little or no response to others. In addition the nature of the immune response can be variable as well. For instance, different fragments of myelin basic protein may have completely opposite effects with some epitopes inducing immune reactivity and other fragments inducing immune suppression (page 107, D. P. Stites and A. I Terr in Basic and Clinical Immunology, Appleton & Lange, Norwalk, Conn., 1991). Therefore, smaller fragments could provide a subset of epitopes compared to the complete antigen. The particular choice and modifications of these fragments can provide more flexibility in the elicitation or alteration of immune responses in a subject. These smaller segments, fragments or epitopes can either be isolated or synthesized.

Antigen dosage can serve as a way of manipulating immunological responses. For example, it has been noted that extremes in dosage of some antigens induce immune suppression whereas a range of dosages in between induces immune reactivity. Thus the same set of antigenic epitopes are capable of invoking-either of two opposite results. Furthermore, even when the same response evoked it can be by two different pathways. For instance, with regard to, oral tolerance, high dosages have been linked to a clonal deletion mode of induction whereas low dosages have been identified with the induction of suppressor cells. (Oral Tolerance: Mechanisms and Applications, H. L. Weiner and L. F. Mayer, eds. Annals of the New York Academy of Sciences Volume 778).

Methods that can be used to introduce an antigen or antigens into a subject may comprise but are not limited to intramuscular, intravenous, and intrathymic injection, nasal inhalation, oral feeding and gastral intubation. In addition to administration of antigen to a subject to induce, a desired immune response in a subject, the desired immune response or responses themselves may be introduced into the subject. This can be carried out by a process that has been termed adoptive transfer. The particular immune cells used for the transfer may have originated from the subject (autologous transfer) or they may be from a syngeneic or non-syngeneic donor (non-autologous transfer). The storage, growth or expansion of the transferred immune cells may have taken place in vivo or in vitro.

Methods for in vivo storage, growth or expansion of cells of a subject in a surrogate host prior to reimplantation have been described in U.S. patent application Ser. No. 08/876,635 filed on Jun. 16, 1997). Methods for in vitro storage, growth or expansion of cells prior to transfer are well known to practitioners of the art. When the immune cells intended for use in a transfer are derived from a donor, these cells may also undergo storage, growth or expansion in vivo or in vitro as described above. Immune cells that are to be transferred may be naïve or they may have been exposed to an immunological reagent such that they are immune reactive, immune suppressive or as described previously, a mixture of both. In vivo methods can be used to introduce an immunological reagent to a surrogate host or a donor in order to render immune cells immune reactive and/or immune suppressive toward a specific antigen or antigens.

In addition, prior to implantation immune cells can be rendered immune reactive and/or immune suppressive by exposure of the immune cells to at least one specific antigen during in vitro conditions. Such conditional or adoptive immune training would provide immune cells with immune responsiveness towards at least one specific antigen. In addition the immune cells may be genetically modified by any of a number means known to those skilled in the art. These modifications can include but not be limited to genetic editing (Wetmur et al., U.S. Pat. No. 5,958,681) and capability of anti-sense (Inouye et al., U.S. Pat. No. 5,272,065) or gene expression. Antisense expression can include but not be limited to resistance to virus infection and elimination of native gene expression. An example of anti-sense to native gene expression would include but not be limited to major histocompatibility (MHC) genes. Gene expression that is conferred by genetic manipulation can include expression of native or non-native gene products. These may include but not be limited to antibodies, growth factors, cytokines, hormones, and drug resistance.

The immune cells may be used as a mixture or sub-populations may be segregated or isolated for use. For instance, it may be desirable to separate out immune reactive cells such as $CD4^+$, $CD8^+$ or $CD34^+$ or other cells. In another example, in a population of immune reactive cells it may be desirable to isolate immune cells that synthesize one particular form of antibody from immune cells that synthesize other forms or immune cells that are cytotoxic to cells expressing one or more specific cell surface markers. When the source of the cells used for adoptive transfer are not native to the subject but are from a donor (non-autologous transfer), additional steps may be required for successful implantation. Such treatments can comprise partial or total ablation of the subjects immune system prior to transfer or the use of immune suppressive drugs. Alternatively or in combination, the subject can further be treated to manage Graft versus Host complications as described in U.S. patent application No. 08/808/629 supra.

In the present invention, auxiliary treatments may also in conjunction with introduction of an antigen or antigens to the subject. For example, provision of adjuvants, immunosuppressive reagents, anti-inflammatory reagents and cytokines can all be used in conjunction with the present invention by shifting various components of the immune response.

The present invention has been described in terms of accomplishment of a binary response by means of a single mode of treatment. In another aspect of the present invention; more than one therapeutic treatment is carried out either sequentially or simultaneously. Thus, one can use one or more treatments that are anticipated increase immune reactivity towards one or more epitopes or antigens and one or more treatments that are anticipated to decrease immune reactivity towards one or more epitopes or antigens. Thereby a new immune state can be achieved where the various elements and components that comprise the sets of immune reactions and immune suppressions have been enhanced or diminished.

Understanding the duality of the immune response allows the prediction that after cessation of treatment there may be a reversion to a state that is closer to the pretreatment immune states. To manage such a potential reversion, the subject may be maintained continuously under treatment or alternatively the treatment can be carried out periodically. The timing of periodic treatments can be carried out at set intervals or may be determined by observations of the onset of immune reversion. During continuous or periodic treatment, the mode of the treatment, the nature of the antigen or the dosage may stay the same or they may be varied as needed.

Thus, contrary to prior art, the present invention predicts that a change in immunological state (through manipulation) does not have to be unidirectional but may lead to a dual or multi changes in opposite directions (increase and decrease in one or more components in the immune response toward an antigen or antigens. By this manipulation, it is possible to reduce the undesirable aspects or components of the immune response that may be the underlying cause or a contributory factor to disease development such as destruction of the liver.

DESCRIPTION OF THE PREFERRED EMBODIMENTS

EXAMPLE 1

Materials and Methods

Fifteen subjects were enrolled in the clinical study. The subjects were men or women with a diagnosis of active HBV infection (acute or chronic) based on liver biopsy (active inflammatory response), and positive for HBsAg with liver enzymes at least twice above normal. The subjects were required to meet one or more of the following criteria: (1) failed treatment with interferon or were unable to receive interferon; (2) hepatocellular carcinoma and active inflammatory response; (3) fulminant liver failure or severe deteriorating synthetic liver functions; (4) liver transplant recipient with evidence of reinfection of the graft and active inflammatory reaction in the liver, who failed or were unable to receive interferon or lamivudine; and (5) had HBV immune mediated disease (i.e., cryo, PAN, neuropathy, kidney involvement).

The subjects were fed with recombinant HbsAg preS1+ preS2 twice a day for 20 weeks. The HBV antigen was given in liquid form, diluted in calf serum. The subjects were given 1 tablet of Omeprazole (20 mg/day/orally) 4 hours before the HBV antigen to prevent the effect of gastric acidity on the ingested antigen.

The subjects were followed for 20 weeks of feeding and 20 weeks after completion of feeding. The subjects were tested every other week for the 20 weeks of feeding and continued monthly for 20 weeks after feeding. A liver biopsy was performed before the study began and again after completion of the 20-week feeding period. The biopsies were stained using the standard hematoxylin and eosin (H&E) stain. HB surface antigen and HB core antigen were determined using immunohistochemical staining techniques. Liver enzymes, ALT and AST levels were followed bimonthly. HBV DNA (viral load) was quantified bimonthly using PCR.

Cytotoxic lymphocyte response and specific T-cell activity to HB surface antigen determined by a T-cell proliferation assay were assayed as described (Chisari et al., "Hepatitis B virus immunopathogenesis"; Ann. Rev. Immunol. 13:29-45 (1995); Rehermann et al., "Cytotoxic T lymphocyte responsiveness after resolution of chronic hepatitis B virus infection," J. Clin. Invest. 7:1655-1665 (1996); Guidotti et al., Viral clearance without destruction of infected cells during acute HBV infection; Science 284:825-829 (1999); Ishikawa et al., "Polyclonality and multispecificity of the CTL response to a single viral epitope;" J. Immunol. 161:5842-5850 (1998)).

The number of specific T-cell clones secreting IFN γ when exposed to HB surface antigen was measured by an ELISA Spot Assay (Hauer et al., "An analysis of interferon gamma, IL-4, IL-5 and IL-10 production by ELISPOT and quantitative reverse transcriptase-PCR in human Peyer's patches;" Cytokine 10:627-634 (1998); Larsson et al., "A recombinant vaccinia virus based ELISPOT assay detects high frequencies of Pol-specific CD8 T cells in HIV-1-positive individuals;" AIDS 13:767-777 (1999)).

IFN γ and IL 10 were quantified using RT PCR (Ilan et al., "Insertion of the Adenoviral E3 region into a recombinant viral vector prevents antiviral humoral and cellular immune responses and permits long term gene expression;" Proc. Nat. Acad. Sci. (USA) 94:2587-2592. (1997); Ilan et al., "Oral tolerization to adenoviral antigens permits long term gene expression using recombinant adenoviral vectors;" J. Clin. Invest. 99:1098-1106 (1997)). Specific serum cytokines were measured as described by Ilan et al. (Ilan et al., "Treatment of experimental colitis by oral tolerance induction: a central role for suppressor lymphocytes;" Am. J. Gastroenterol. 95:966-973 (2000)).

Analysis of Results

Patients were considered to have reacted positively to the hepatitis B virus antigens if they demonstrated one or more indications of a decrease in a specific immune response and one or more indications of an increase in a specific immune reaction.

Indications of a decrease in a specific immune response can be one or more of the following:
1) Decrease in one or both enzyme (ALT and/or AST) levels;
2) Decrease (improvement) in liver pathology as measured by standard hemotoxylin & eosin (H&E) staining;
3) Decrease in HB surface antigen staining by immunohistochemistry; and
4) Decrease in HB core antigen staining by immunohistochemistry.

Indications of an increase in a specific immune reaction can be one or more of the following:
1) Decrease in viral load by PCR;
2) Increase in specific T cell activity to HB surface antigen as measured by a T-cell proliferation assay (T-cell assay);
3) Increase in number of specific T-cell clones secreting IFN γ when exposed to HB surface antigen as measured by an ELISA Spot Assay;
4) Increase in IFN γ and/or IL 10 as measured by RT PCR;
5) Increase in cytotoxic lymphocyte response; and
6) Increase in specific serum cytokines.

TABLE 1

Summary of Immune Reactions

| Subject | Decrease in Specific Immune Response | Increase in Specific Immune Reaction |
|---|---|---|
| 502 LA | ALT levels decreased | Viral load decreased<br>T-cell proliferation increased<br>Specific T-cell clones secreting<br>IFN γ (ELISA spot assay) increased |

TABLE 1-continued

Summary of Immune Reactions

| Subject | Decrease in Specific Immune Response | Increase in Specific Immune Reaction |
|---|---|---|
| 503 RM | Not fully responding yet | Viral load decreased<br>Cytotoxic lymphocyte response increased |
| 506 ASA | Liver pathology (H&E) decreased<br>HB core antigen staining decreased | T-cell proliferation increased |
| 509 II | ALT levels decreased | T-cell proliferation increased<br>Specific T-cell clones secreting<br>IFN γ (ELISA spot assay) increased |
| 511 EBH | ALT levels decreased<br>AST levels decreased<br>Liver pathology (H&E) decreased<br>HB surface antigen decreased<br>HB core antigen staining decreased | Viral load decreased<br>T-cell proliferation increased<br>Specific T-cell clones secreting<br>IFN γ (ELISA spot assay) increased<br>IFN and IL 10 positive by RT PCR<br>Cytotoxic lymphocyte response increased |
| 517 FA | HB surface antigen decreased<br>HB core antigen staining decreased | Viral load decreased<br>T-cell proliferation increased<br>Specific T-cell clones secreting<br>IFN γ (ELISA spot assay) increased |
| 518 IZ | HB core antigen staining decreased | Viral load decreased<br>T-cell proliferation increased<br>Specific T-cell clones secreting<br>IFN γ (ELISA spot assay) increased<br>IFN and IL 10 positive by RT PCR |
| 520 YB | AST levels decreased | T-cell proliferation increased<br>Specific T-cell clones secreting<br>IFN γ (ELISA spot assay) increased<br>IFN and IL 10 positive by RT PCR |
| 505 NS | ALT levels decreased<br>AST levels decreased<br>HB core antigen staining decreased | Viral load decreased<br>T-cell proliferation increased<br>Specific T-cell clones secreting<br>IFN γ (ELISA spot assay) increased |
| 519 KS | ALT levels decreased<br>AST levels decreased<br>HB surface antigen staining decreased | T-cell proliferation increased<br>Specific T-cell clones secreting<br>IFN γ (ELISA spot assay) increased<br>IFN and IL 10 positive by RT PCR |
| 513 PW | Liver pathology (H&E) decreased<br>HB surface antigen staining decreased<br>HB core antigen staining decreased | T-cell proliferation increased<br>Specific T-cell clones secreting<br>IFN γ (ELISA spot assay) increased<br>IFN and IL 10 positive by RT PCR |
| 514 TY | ALT levels decreased<br>AST levels decreased<br>Liver pathology (H&E) decreased<br>HB surface antigen staining decreased<br>HB core antigen staining decreased | Viral load decreased<br>T-cell proliferation increased<br>IFN and IL 10 positive by RT PCR |
| 515 JH | ALT levels normal<br>AST levels normal | T-cell proliferation increased<br>Specific T-cell clones secreting<br>IFN γ (ELISA spot assay) increased<br>IFN γ in serum increased |
| 504 GE | Liver pathology (H&E) decreased<br>HB surface antigen staining decreased<br>HB core antigen staining decreased | T-cell proliferation increased<br>Specific T-cell clones secreting<br>IFN γ (ELISA spot assay) increased<br>IFN and IL 10 positive by RT PCR<br>Cytotoxic lymphocyte response increased |
| 521 MH | Liver pathology (H&E) decreased | T-cell proliferation increased<br>Specific T-cell clones secreting<br>IFN γ (ELISA spot assay) increased<br>IFN and IL 10 positive by RT PCR |

In some subjects the specific response was reversed after treatment. This may indicate that the effect of treatment may be transient and/or reversible and continued or repeated treatment may be recommended.

In the subjects introduction of hepatitis B surface antigen achieved a dual effect, exhibiting an increase in at least one aspect of the immune reaction towards HBV while exhibiting a decrease in at least one aspect of the immune reaction towards HBV or hepatocytes.

EXAMPLE 2

Materials & Methods:

Mice: Female immunocompetent (heterozygous) and athymic Balb/c mice were purchased from Jackson Laboratories, Bar Harbor, Me. All animals were kept in laminar flow hoods in sterilized cages, receiving irradiated food and sterile acidified water as described (Shouval at al., "Comparative morphology and tumorigenicity of human hepatocellular cell carcinoma lines in athymic rats and mice;" *Vichow's Archives A. Path. His.* 412:595-606, (1988)).

Cell cultures: The human hepatoma cell line Hep-3B which secretes HBsAg was grown in culture as a monolayer, in medium supplemented with non essential amino acids and 10% heat inactivated fetal bovine serum as described (American Type Culture Collection, ATCC, HB-8064, HB-8065; Shouval et al., *Vichow's Archives A. Path. His.*, supra;).

Induction of anti-HBV immune response: BioHepB recombinant hepatitis B vaccine (BioTechnology General LTD, Israel) which contains three surface antigens of the hepatitis B virus: HBsAg, PreS1 and preS2, was used for induction of anti-HBV immune response. Immunocompetent Balb/c donor mice were immunized against HBV with 1 μg HBsAg intraperitonealy (i.p.) at one month, followed by a boost vaccine one week before splenocyte transplantation.

Preparation of HCC antigens: HCC cells were used as tumor associated antigens. After growth in cell cultures, the cells were filtered through a 40 m nylon cell strainer. The intact cells were spun down and removed. Proteins were quantified using a protein assay kit (BioRad Laboratories, Hercules, Calif.).

Oral administration of HCC cells or HBV antigens: Hep-3B cells (50 g protein) expressing HBsAg or recombinantly prepared HBsAg+PreS1+PreS2 antigens (BioHepB, Bio-Technology General LTD, Israel) or low dose HBV antigens (BioHepB, 1 mcg) were administered orally. The antigens were administered with a feeding atraumatic-needle, on alternate days for 10 days (a total of 5 doses) prior to HBV vaccine immune induction. A control group received similar doses of bovine serum albumin (BSA).

Assessment of anti-HBs humoral immune response: Mice in all groups were followed for anti-HBs antibody titers at sacrifice (prior to splenocyte transplantation) 30 days following inoculation of the BioHepB vaccine, 7 days following the boost vaccination. HBs antibodies were measure by a commercial solid phase radioimmunoassay (RIA).

Tumor and splenocyte transplantation in athymic mice: Athymic mice were used as splenocyte recipients and conditioned with sub-lethal radiation (600 cGy). Twenty four hours after irradiation, the animals were injected subcutaneously in the right shoulder with $10^7$ human hepatoma Hep3B cells as described in Shouval et al. infra (Shouval et al., "Adoptive transfer of immunity to hepatitis B virus in mice following bone marrow transplantation through immunization of bone marrow donors:" *Hepatology* 17:955-959 (1993)). Seven days after irradiation, athymic mice received splenocyte transplantation as follows: on transplantation day; donor mice were sacrificed and spleens were harvested. Splenocyte recipients were then injected I.V. with spleen cells at $2 \times 10^8$ cells/mouse (Shouval et al., *Hepatology*, supra).

Follow-up of tumor growth: Recipient mice were followed at weekly intervals for 2 months with monitoring of tumor growth by calipers, and periodic serum measurements of HBsAg and alfa-fetoprotein (AFP) levels. Blood samples were obtained weekly by retrobulbar puncture and serum was separated and frozen at −20° C. until assayed by a commercial solid phase radioimmunoassay (RIA).

Cytokine production: To evaluate the effect of immune reactivity on the balance of pro-inflammatory and anti-inflammatory cytokines, TNF, IFN IL2, TGF and IL10 mRNA production were measured periodically in recipient mice by RT-PCR. Serum levels of the cytokines were measured by a highly sensitive RIA according to the manufacturers' instructions.

Radioimmunoassays for detection of serum HBsAg, anti-HBs and aloha-feto-protein: HBsAg and antibodies to HBsAg were determined by commercial solid phase RIA (Ausria II and Ausab, Abbott Laboratories, North Chicago, Ill.; R&D Systems, Minneapolis, Minn.). A World Health Organization reference serum was used for quantitative analysis of anti-HBs by RIA, utilizing the Hollinger formula and data expressed in mIU/ml (Hollinger at al., "Improved double antibody radioimmunoassay (RIA-D) methodology for detecting hepatitis B antigen and antibody." (Abstract), *Am. Soc. Microbiol.* 72:213(1972)). Alpha feto protein (AFP) was measured by RIA (AFP, Bridge Serono, Italy) and expressed in ng/ml.

Experimental Groups: Donor mice were divided into 4 groups of 10 mice each (Table 2). Groups A to C received oral feedings prior to HBV vaccine. Experimental group A received oral feedings of Hep3B hepatoma cells. Experimental group B received oral feedings of HBV antigens. Control group C received oral feedings of BSA (Table 2). The above groups received HBV vaccination as described. Control group D was neither vaccinated nor fed antigens. Recipient mice consisted of 4 parallel groups A to D and received injections of Hep3B cells as described above and then received splenocytes from the donor mice.

TABLE 2

Experimental groups.

| Group: | Donor mice: Immunization to HbsAg | Donor mice: Oral feedings |
|---|---|---|
| A | Immunized | Hep3B hepatoma cells |
| B | Immunized | HBV antigens |
| C | Immunized | BSA |
| D | None | None |

Analysis of Results:

Evaluation of the effect of oral administration of HCC proteins or HBV antigens on anti-viral humoral immune response: The effect of oral feedings of HCC extracted proteins expressing HBsAg or HBV antigens on anti-HBV peripheral immune reactivity was evaluated by measuring serum anti-HBsAg antibody production. This was measured at sacrifice—prior to splenocyte transplantation, 30 days following inoculation of the BioHepB vaccine and 7 days following a boost vaccination. Administration of HCC extracted proteins markedly decreased the anti-viral humoral immune response. A lesser degree of decrease was evident in mice exposed to HBV antigens. At sacrifice, 30 days following inoculation with the vaccine, serum anti-HBs antibody levels were 157±271 vs. 382±561 and 664±757 mIU/ml in HCC fed mice, (group A), compared with HBV-envelope proteins fed mice (group B) and BSA-fed controls (group C), respectively ($p<0.05$ between groups A and C.

Effect of adoptive transfer of HBV immunity on tumor growth as manifested by tumor volume and serum AFP levels:

Tumor growth was suppressed completely in mice that received splenocytes immunized to HBsAg (group C). After transplantation, no tumor grew and there was no macroscopic evidence of tumor growth. This correlated with AFP serum levels that were negative for the duration of the experiment (12 weeks).

Tumor growth was significant in mice that received naive splenocytes (group D) and the mice had big tumors after 2 weeks of tumor transplantation. Tumor growth was rapid and tumor size was 151±78 mm$^2$ and 165±24 mm$^2$ at 2 and 4 weeks respectively $p<0.0001$ between groups C and D). This correlated with AFP serum levels that rose in parallel to tumor growth. AFP serum levels were 2320±2123 ng/ml and 2500±1431 ng/ml at 2 and 4 weeks respectively p<0.02 between groups C and D). Due to enormous tumor size after 4 weeks and deterioration in general state of these mice with 25% mortality, they were sacrificed.

Effect of oral administration of HBV or HCC proteins on tumor growth as manifested by tumor volume and serum AFP levels:

Mice receiving splenocytes from mice fed HCC extracted proteins (group A) showed only transient tumor growth. While tumor growth was not evident macroscopically, AFP serum levels were significantly elevated after two weeks and declined thereafter and were negative after 6 weeks. AFP serum levels were 574.4±539 ng/ml and 418±520 ng/ml at 2 and 4 weeks respectively. This was significant compared to mice immunized against HBV (group C); p<0.02 between groups A and C).

Mice receiving splenocytes immunized against HBV and exposed to oral feedings of HBV antigens (group B) had no evidence of tumor growth. No evidence of macroscopic tumor growth or rise in serum AFP levels was seen in these mice.

Effect of tumor growth on weight gain, mortality and general appearance in the various groups: Mice that received HBV immunized splenocytes and completely suppressed tumor growth with no evidence of tumor growth showed continued weight gain throughout the 12 week experiment (group C). This was in contrast to mice receiving naive splenocytes (with significant tumor growth) that had in parallel a significant reduction in body weight (group D). This body weight loss became worse during the 4 weeks of follow-up and correlated with tumor growth, general deterioration and mortality. Body weight in these mice was significantly reduced as compared with mice in group C. Body weight was 17.7±1.8 and 20.7±1.3; respectively at 2 weeks (p<0.003) and 17.1±18 gr 21.4±0.6 gr respectively at 3 weeks (p<0.00004). Mice in group C that did not show tumor growth appeared well and there was no mortality throughout the 12 week follow-up. This was in contrast to mice in group D (that showed tumor growth) that appeared extremely sick, performed poorly and had a mortality rate of 12.5% after 2 weeks and 25% after 3 weeks.

Mice receiving splenocytes from mice led HCC extracted proteins (group A) that showed transient tumor growth had in parallel an initial reduction in body weight that was significantly lower that group C mice that did not have tumor growth. A similar but less significant reduction in weight was evident in mice receiving splenocytes immunized to HBsAg and exposed orally to HBV antigens (group B). Body weights were 16.2±2.0 and 17.8±2.4 in groups A and B respectively at 2 weeks (p<0.0006; P<0.01 respectively compared to group C) and 18.5±1.9 gr and 18.5±2.0 gr respectively at 4 weeks (p<0.002; p<0.003 compared to group C). No significant difference in body weight was evident between groups A, B and D during the four weeks. After 4 weeks there was gradual increase in body weights in groups A and B that correlated with tumor suppression in group A as evident by negative AFP levels in this group. Mice in groups A and B initially looked sick in correlation with weight loss and had an early mortality rate at 4 weeks of 40% in both groups. However, after four weeks these mice were looking better and although they did not look as healthy as mice in group C there was some improvement in their general appearance and performance. After 4 weeks there was no mortality in these groups, similar to group C.

Effect of tumor growth on cytokine profile:

Mice in group A that received splenocytes from HCC-fed mice had elevated levels of interferon gamma production evident by RT-PCR of splenocytes. Lesser levels were evident in group B. This was in contrast to group C (that had no tumor growth) that had no evidence of interferon production in splenocytes by RT-PCR.

TABLE 3

Anti-HCC Immune Response

| Adoptive Transfer of Splenocytes | Tumor Growth | Tumor Suppression | | Tumor Promotion | |
|---|---|---|---|---|---|
| | | Activated anti HBV | Non-Specific Anti-Tumor | Towards HBV | Non-specific |
| Anti HBV Immunized | − | +1 | + | + | + |
| Anti HBV Immunized Orally fed with HBV antigens | − | +2 | + | − | − |
| Anti HBV Immunized Orally fed with HCC antigens | − | +3 | | − | − |
| Naive | + | − | | + | + |

Many obvious variations will no doubt be suggested to those of ordinary skill in the art in light of the above detailed description and examples of the present invention. All such variations are fully embraced by the scope and spirit of the invention as more particularly defined in the claims that now follow.

What is claimed is:

1. A method for treating chronic or acute HBV infection in a subject, comprising orally administering an effective amount of HBV antigen to said subject.

2. The method of claim 1, wherein the treatment results in a response selected from the group consisting of decreased ALT level, decreased liver pathology, decreased AST level, decreased HB surface antigen, and decreased HB corn antigen.

3. The method of claim 1, wherein the treatment results in a response selected from the group consisting of decreased viral load, increased T-cell proliferation in response to HBV antigen, increased T-cell secretion of IFN γ in response to HBV antigen, increased CTL against HBV antigen, increased IFN γ and IL-10 gene expression, and increased serum IFN γ.

4. The method of claim 1, where the HBV antigen is HbsAG preS1+preS2.

5. The method of claim 1, where said subject is treated to prevent gastric acidity before administering the HBV antigen.

6. The method of claim 1, where the antigen is administered twice a day.

7. The method of claim 6, where the antigen is administered for 20 weeks.

* * * * *